United States Patent
Bergbreiter et al.

(10) Patent No.: US 9,370,770 B2
(45) Date of Patent: Jun. 21, 2016

(54) NONPOLAR PHASE-SOLUBLE METATHESIS CATALYSTS

(71) Applicant: The Texas A&M University System, College Station, TX (US)

(72) Inventors: David E. Bergbreiter, College Station, TX (US); Hassan S. Bazzi, Doha (QA); Chayanant Hongfa, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 96 days.

(21) Appl. No.: 14/261,150

(22) Filed: Apr. 24, 2014

(65) Prior Publication Data

US 2015/0057449 A1 Feb. 26, 2015

Related U.S. Application Data

(63) Continuation of application No. 12/286,745, filed on Oct. 1, 2008, now abandoned.

(60) Provisional application No. 60/997,093, filed on Oct. 1, 2007.

(51) Int. Cl.

| | |
|---|---|
| *B01J 31/16* | (2006.01) |
| *C07D 207/48* | (2006.01) |
| *C07D 211/96* | (2006.01) |
| *C07C 67/30* | (2006.01) |
| *C07C 67/333* | (2006.01) |
| *C07D 233/58* | (2006.01) |
| *C07D 295/24* | (2006.01) |
| *C07D 403/14* | (2006.01) |
| *C08L 65/00* | (2006.01) |

(52) U.S. Cl.
CPC ............ *B01J 31/1683* (2013.01); *C07C 67/30* (2013.01); *C07C 67/333* (2013.01); *C07D 207/48* (2013.01); *C07D 211/96* (2013.01); *C07D 233/58* (2013.01); *C07D 295/24* (2013.01); *C07D 403/14* (2013.01); *C08L 65/00* (2013.01); *B01J 2231/543* (2013.01); *B01J 2531/17* (2013.01); *B01J 2531/821* (2013.01); *C07C 2101/10* (2013.01); *C07C 2101/16* (2013.01); *C08G 2261/418* (2013.01)

(58) Field of Classification Search
CPC ............ B01J 31/1683; B01J 2231/543; B01J 2531/17; B01J 2531/821; C07C 67/30; C07C 67/333; C07C 2101/10; C07C 2101/16; C07D 207/48; C07D 211/96; C07D 233/58; C07D 295/24; C07D 403/14; C08L 65/00; C08G 2261/418
USPC ........... 526/171; 546/339; 548/542; 560/122, 560/128
See application file for complete search history.

(56) References Cited

U.S. PATENT DOCUMENTS 3,220,972 A 11/1965 Lamoreaux

FOREIGN PATENT DOCUMENTS

JP 10176156 * 6/1998 ............. C09J 123/26

OTHER PUBLICATIONS

David E. Bergbreiter, et al., Liquid/Liquid Biphasic Recovery/Reuse of Soluble Polymer-Supported Catalysts, Adv. Synth. Catal. 2006, 348, 1352-1366.
Bogdan Marciniec, et al., Hydrosilylation, Encyclopedia of Catalysis, 2010.
Ray Will, et al., Specialty Chemicals Update Program Adhesive and Sealants, IHS Chemical, Sample Report from 2009.

* cited by examiner

*Primary Examiner* — Ling Choi
*Assistant Examiner* — Chun-Cheng Wang
(74) *Attorney, Agent, or Firm* — Winstead PC

(57) ABSTRACT

One embodiment of the invention provides polyisobutylene (PIB) oligormers that are end-functionalized with ruthenium (Ru) catalysts. Such nonpolar catalysts can be dissolved in nonpolar solvents such as heptane, or any other nonpolar solvent that is otherwise not latently biphasic (i.e., if two or more solvent components are present, they remain miscible with each other throughout the entire reaction process, from the addition of substrate through to the removal of product). Substrate that is dissolved in the nonpolar solvent with the catalyst is converted into product. The lower solubility of the product in the nonpolar solvent renders it easily removable, either by extraction with a more polar solvent or by applying physical means in cases where the product precipitates from the nonpolar solvent. In this manner the catalysts are recycled; since the catalysts remain in the nonpolar solvent, a new reaction can be initiated simply by dissolving fresh substrate into the nonpolar solvent.

6 Claims, 4 Drawing Sheets

US 9,370,770 B2

NONPOLAR PHASE-SOLUBLE METATHESIS CATALYSTS

This application is a continuation of U.S. application Ser. No. 12/286,745, which claims the benefit of priority to U.S. Provisional Application No. 60/997,093, filed Oct. 1, 2007, which is herein incorporated by reference in its entirety.

FIELD OF THE INVENTION

The invention relates to methods and compositions useful for catalyzing chemical reactions. In particular, the invention is drawn to reactions that afford efficient catalyst recycling and reusability. Even more particularly, the compositions and methods provided by the invention relate to the provision of a single nonpolar reaction solvent that is not latently biphasic and a catalyst that is soluble therein.

BACKGROUND OF THE INVENTION

Polymer-supported catalysts are widely used in chemical processes. Much of the technology that is presently available derives from the solid-phase peptide synthesis techniques developed by Merrifield. These techniques are based on insoluble cross-linked polystyrene supports. Catalysts supported on Merrifield resins can be recovered from reaction media using a solid/liquid separation technique such as filtration.

With the growing interest in environmentally friendly, or "green" chemical processes, there is an emphasis on the ability to reuse materials and to minimize amounts of solvents required for a given process. Filtration is typically a relative solvent-intensive process, because the recovered solid is typically rinsed with additional solvent. Further, some polymer-supported catalysts suffer from decreased activity once they are isolated via filtration. This impacts their potential to be reused multiple times.

Soluble polymer-supported catalysts have been developed. These catalysts can be recovered from the reaction medium either by precipitation followed by filtration, by liquid/liquid separation, or by ultrafiltration using a filtration membrane. Precipitation/filtration obviously suffers from the same drawbacks associated with the filtration of insoluble polymer-supported catalysts, described above. Inadequate partitioning of the catalyst into the desired liquid phase often impairs liquid/liquid separations. For example, liquid/liquid separation is impractical if the catalyst and the product are both soluble in the same phase. Ultrafiltration of soluble catalysts using membranes has enjoyed some success, but the recycled catalysts often suffer from some loss of activity.

An alternative way of using a soluble catalyst is to use a biphasic system wherein the catalyst is preferentially soluble in one phase and the substrate and/or products are soluble in the other phase. To allow the reaction to proceed using this setup, the biphasic solvent system is vigorously mixed to ensure maximum contact between the catalyst and substrate. After the reaction, the mixture is allowed to settle and the product phase is removed, leaving the catalyst phase available for more reactions. This constitutes an example by which the soluble catalyst is recycled. The drawback to biphasic systems is that the presence of multiple phases introduces kinetic barriers to reaction. Such barriers result for the lack of solubility of both the catalyst and substrate in the same reaction solvent, which lowers the interaction rate between these reaction components.

The drawbacks associated with biphasic solvent systems can be overcome by using a solvent system that is monophasic under one set of conditions and biphasic under a different set of conditions. For example, liquid-liquid biphasic systems that exhibit an increase in phase miscibility at an elevated temperature and incorporate soluble polymer-bound catalysts having a strong phase preference at ambient temperature have been described by Bergbreiter and colleagues (2000, 2001; both references of which are herein incorporated by reference in their entirety).

Such thermomorphic biphasic reaction systems are also referred to as latent biphasic reaction systems, which are described in U.S. Pat. No. 7,211,705 (incorporated herein by reference in its entirety). This publication describes other latent biphasic reactions where conditions such as ion concentration are modified to effect the switch from the biphasic state (i.e. two or more solvents are immiscible) to the monophasic state in which the solvents become miscible with one another, creating a heterogeneous solvent. Upon reaction completion, the biphasic state (or multiphasic state) must be restored in order to regain access to catalyst apart from the product. Consequently, latent biphasic solvent systems can be rather complex, necessitating the empirical determination of conditions that will effectively govern a reversible phase transition allowing i) effective mixing of catalyst with substrate, and ii) separation of catalyst from product.

A process that is similar to the above-described latent biphasic systems has previously been described (Bergbreiter et al., 2003). In that process, substrate and soluble catalyst are initially dissolved in a homogeneous solvent containing at least two different solvents. The conditions are such that only a slight modification, or perturbation, of the reaction system will result in the immiscibility and separation of the different solvents (i.e. the system is partly latently biphasic). The strategy in this case is to ensure that the catalyst and reaction product are not greatly soluble in the same solvent after system perturbation. Shared solubility obviously impedes acquisition of pure catalyst.

In view of the prior art, there remains a need for catalytic methods that allow for the efficient separation of the catalyst from the reaction product and the recycling of the catalyst. Further, there is a need for such methods wherein the recycled catalyst is highly reusable. It is desirable that such methods operate with minimal additional solvent to effect the separation of the catalyst.

SUMMARY OF THE INVENTION

One embodiment of the present invention is directed to a reaction composition that comprises a nonpolar solvent that is not latently biphasic, a catalyst that is complexed to a nonpolar support (i.e., catalyst-support complex), and a molecule that is a substrate for the catalyst. With this embodiment, the catalyst-support complex and substrate molecule are both dissolved in the nonpolar solvent; however, the product of the reaction is less soluble in the solvent compared to the molecule. In other embodiments of the composition, the product is completely insoluble in the solvent. The partial or complete insolubility of the product in the reaction solvent, coupled with the complete solvency of the catalyst-support complex, allows for the facile separation of the product from the catalyst; the latter component can thus be recycled for another round of substrate-to-product conversion.

Certain embodiments of the reaction composition incorporate a nucleophilic organic group as the catalyst. An example of such a catalyst would be a type of a triorganophosphine. In other embodiments, the catalyst comprises an imidazole group, thiazole group, or pyridine group. The catalyst of the present invention can also be, more generally, a hydrocarbon, a hydrocarbon containing one or more ester groups, a hydrocarbon containing one or more ether groups, or a hydrocarbon containing one or more amine groups. The catalyst can also comprise a metal; examples include ruthenium and silver.

The nonpolar support of the inventive composition can comprise, for example, polyisobutylene, polyethylene, poly (N-octadecylacrylamide), polysiloxane, polyamidoamine, poly(1-alkene), or polypropylene. An N-heterocyclic carbene moiety or benzylidene moiety, for example, can be used to bridge the catalyst to the support. Components that are chosen to attach to the support and act as a ligand for the catalyst should not impede the ability of the resulting catalyst-support complex to dissolve in a nonpolar solvent.

In other embodiments of the inventive composition, the solvent incorporated therein is toluene, dichloromethane, dibutyl ether, or an alkane. A preferred embodiment incorporates heptane. Some embodiments comprise a single solvent component, whereas other embodiments comprise a mix of one or more solvents. In the latter case, the solvent mix should not be latently biphasic under the conditions (e.g., temperature, salt, pressure) employed during the reaction. Indeed, the present invention may incorporate solvent mixtures that have the potential to behave in a latent biphasic manner; however, such incorporation in the present invention is only under reaction conditions that do not induce the latent biphasic nature of the chosen solvent mix. In other words, even though the solvent mix used in the invention may be latently biphasic, such a property is not involved in the reaction—the solvent remains monophasic throughout the entire reaction and also during the removal of product.

Certain embodiments of the reaction composition comprise molecules that can be substrates in a ring-closing, ring-opening, or cross metathesis polymerization reaction. Preferred embodiments employ substrates that can undergo ring-closure.

In a particularly preferred embodiment of the instant invention, the reaction composition comprises heptane as the solvent, a ruthenium catalyst that is in complex with a polyisobutylene-containing support, and a heptane-soluble substrate molecule. In this embodiment, the catalyst-support complex is heptane-soluble, and the substrate molecule is a substrate for ruthenium. The product of the reaction occurring between the ruthenium catalyst and substrate has little or no solubility in heptane. This feature permits facile separation of the product from the catalyst, the latter of which can then be used in a reaction with newly added substrate. Certain aspects of this embodiment may also incorporate an N-heterocyclic carbene moiety as a bridge between the polyisobutylene support and the ruthenium complex.

The instant invention is also drawn to a method of catalyzing a chemical reaction having the steps of providing a reaction composition as described above, allowing the substrate molecule to be catalyzed into product, and separating the product from the reaction composition. The product separation step can be performed in different ways. One strategy for separation is through the use of physical means, such as siphoning, filtering, or decanting, all of which can be employed if the product is nearly or totally insoluble in the solvent. Another strategy for separation is through extraction of the product by adding and removing a second solvent to the reaction composition; the second solvent can be a polar organic solvent such as acetonitrile, for example. In this latter aspect of the inventive method, the product is preferably soluble in the second solvent compared to the nonpolar solvent of the reaction composition. Throughout either process (physical separation or extraction), the catalyst-support complex remains dissolved in the nonpolar solvent. This feature allows for the step of reusing the catalyst-support complex by dissolving fresh substrate into the nonpolar solvent.

DETAILED DESCRIPTION OF THE INVENTION

Figure 1:
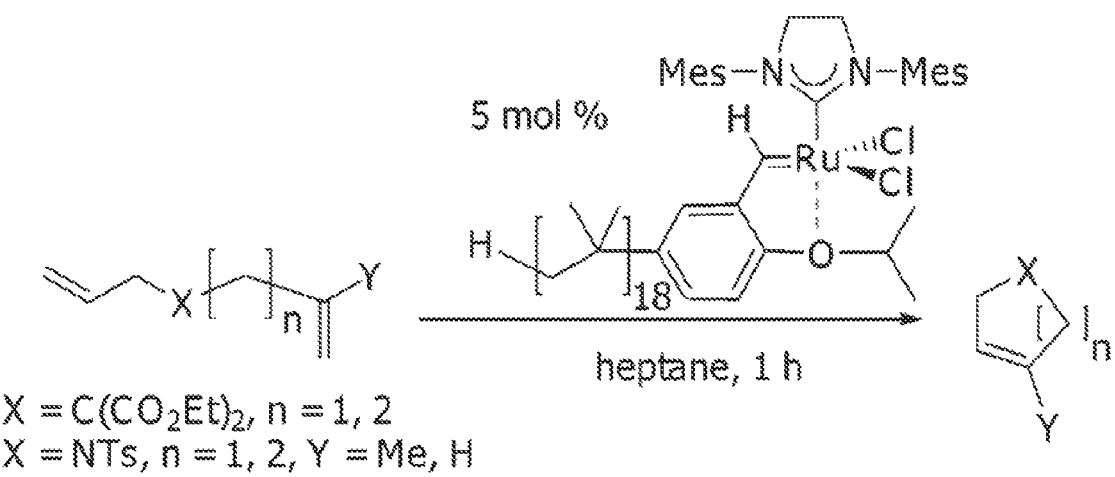
FIG. 1 shows a ring-closing metathesis reaction catalyzed by an end-functionalized polyisobutylene (PIB)-bound Ru metathesis catalyst. Refer to Study 1.

The instant invention provides a catalysis system having a single nonpolar reaction solvent that is not latently biphasic. The solvent may consist of one or more nonpolar liquid components. Solvents consisting of only one component are inherently monophasic and are thus incapable of being latently biphasic. For those solvents having multiple components, the components remain miscible with each other (i.e. remain monophasic) throughout the entire reaction process (i.e. they do not separate to different phases upon some form of manipulation), from the addition of substrate to the removal of product. This system thus does not necessitate the provision of latent biphasic reaction schemes, which involve rather complex manipulations (e.g. specific temperature or ionic state changes). The inventive reaction scheme allows for the catalyst and substrate to be soluble in the single nonpolar solvent. Surprisingly, the reaction products are easily separated from the nonpolar solvent by virtue of the products' own lack or lower degree of solubility therein, which permits efficient recycling of the catalyst. This key feature distinguishes the present invention from other monophasic systems. Product removal can be performed by simple isolation of reaction precipitate, or in cases where the product does not readily fall out of solution from the nonpolar solvent, by introducing a second solvent that is immiscible with the reaction solvent and capable of solvating the product but not the catalyst. Importantly, neither of these separation steps involve manipulating the catalyst itself (e.g., mobilizing the catalyst from one solvent to another); consequently, enhanced catalyst reusability characterizes the enhanced recycling provided by the instant invention.

The instant invention incorporates one or a mixture of nonpolar solvents in which the above reaction takes place. Such solvents include, for example, hydrocarbon solvents such as toluene, benzene and xylene (i.e. aromatic solvents), and saturated hydrocarbons such as propane, butane, pentane, hexane, cyclohexane, heptane, octane, nonane, decane and dodecane, which may also be used in branched form. Other nonpolar solvents include mineral oils, natural oils and synthetic oils as well as mixtures thereof. Still other nonpolar solvents useful in practicing the instant invention are dichloromethane and dibutyl ether.

The instant invention incorporates a nonpolar support which is soluble in a nonpolar solvent. During the course of the inventive reaction process, the support remains dissolved in the nonpolar solvent. Non-limiting examples of materials/polymers suitable for preparing the support are polystyrene, polycarbonate, polyacrylates, polylactic acid, polyglycolic acid, polycaprolactone, polyisobutylene, polyethylene, poly (N-octadecylacrylamide), polysiloxane, polyamidoamine, poly(1-alkene), polypropylene, polymethyl(meth)acrylate, polyethyl(meth)acrylate and polybutyl(meth)acrylate. In general, oil-soluble polymers can be used as support materials. The support can comprise one or more different materials.

With respect to solubility of the various components of the invention (e.g., catalyst-support complex, substrate molecule, product molecule), "soluble" is defined as when a mixture (e.g., substrate in nonpolar solvent) is homogeneous, not turbid, and without substantially any undissolved residue; whereas "insoluble" is defined as when a mixture (e.g., product in nonpolar solvent) is not homogeneous or is overly turbid. Partial solubility refers to when parts of the material remain solid or in a gel form when attempting to dissolve the material in the solvent.

In certain embodiments of the invention, the catalyst component comprises a nucleophilic organic group. Non-limiting examples of such moieties are phosphines such as triorganophosphines (e.g., triphenylphosphine) and BINAP (2,2'-bis (diphenylphosphino)-1,1'-binaphthyl). The nucleophilic organic group incorporated in the invention can serve to bind certain catalytic metal ligands. Suitable metal catalysts that can be incorporated in the invention include, but are not limited to, iron (Fe), ruthenium (Ru), cobalt (Co), rhodium (Rh), iridium (Ir), nickel (Ni), palladium (Pd), platinum (Pt), copper (Cu), silver (Ag) and other transition metal catalysts familiar to those skilled in the art (e.g., molybdenum, scandium, titanium, vanadium, chromium, manganese, yttrium, zirconium, niobium, technetium, hafnium, tantalum, tungsten, rhenium, osmium, gold, rutherfordium, dubnium, seaborgium, bohrium, hassium, meitnerium, darmstadtium, roentgenium). Other metals useful for practicing the invention are selected from the alkali metals, alkaline earth metals, poor metals, and lanthanoids.

N-Heterocyclic carbene (NHC) groups can be used as moieties to bridge the support with the catalyst. For example, NHC groups can be complexed to a support material, after which the NHC group is used to complex a catalytic metal. For example, NHC groups can be used to form transition metal carbene complexes on the support. Different types of NHC groups that can be incorporated in the instant invention include, for example, imidazol-2-ylidenes (e.g., 1,3-positions functionalized with alkyl, aryl, alkyloxy, alkylamino, or alkylphosphino groups), triazol-5-ylidenes, cyclic diaminocarbenes, and heteroamino carbenes.

Polar organic solvents may be employed when practicing the invention to access certain reaction products that do not readily fall out of solution from the nonpolar solvent. To do so, one would generally employ a standard extraction procedure with the polar organic solvent to separate the product from the nonpolar solvent. When performing such a procedure, the extent to which the catalyst-support complex might transfer from the nonpolar solvent to the polar organic solvent should be determined. Obviously, in order to maximize product purity and minimize catalyst loss, one would choose a polar organic solvent that does not favor phase-transfer of the catalyst-support complex. Different polar organic solvents can be employed when practicing the instant invention such as certain alcohols and ethers. Non-limiting examples of polar organic solvents include methanol, acetonitrile, DMSO, isopropanol, tetrahydrofuran (THF), hexafluoroisopropanol (HFIP), N-methyl-2-pyrrolidone (NMP), dimethylacetamide, N,N-dimethylformamide, 1,2-dimethoxyethane, ethylene glycol, propylene glycol, sulfolanes, and diethylene glycol alkyl ethers (e.g., diethylene glycol monobutyl ether). Other polar organic solvents include amine compounds and alkanolamine compounds (e.g., two carbon atom linkage alkanolamines such as aminoethyleethanolamine [AEEA]).

The present invention is can be employed to carry out different types of reactions, such as ring-closing, ring-opening and cross metathesis polymerization reactions.

EXPERIMENTAL

Study 1

Herein described is an alternative approach using a heptane-soluble polymer to prepare a second-generation Hoveyda-Grubbs catalyst for ruthenium (Ru)-catalyzed metathesis polymerizations that is recoverable and reusable in hydrocarbon solvents by liquid/liquid or liquid/solid separations after catalysis.

Ru-catalyzed ring-closing metathesis, cross metathesis, and ring-opening metathesis polymerization have developed into broadly useful methodologies (Chauvin, 2006; Grubbs, 2006; Trnka and Grubbs, 2001). These homogeneously catalyzed reactions are equally useful in complex syntheses and in the formation of materials. For use in these reactions, end-functionalized polyisobutylene (PIB)-bound Ru metathesis catalysts, which are nonpolar and heptane-soluble, can be transformed from terminally vinyl-functionalized PIB oligomers. FIG. 1 depicts a ring-closing metathesis reaction catalyzed by such a catalyst.

In this example embodiment of the instant invention, it is shown that such nonpolar catalysts can be used to convert substrate into product in a heptane-based reaction solution, and then recycled by simple gravity-based extraction after addition of a heptane-immiscible, more polar solvent. Since the reaction product preferentially dissolves in the more polar solvent, it is mobilized out of the heptane phase, leaving the catalyst available for another reaction cycle. Further demonstrated by this invention embodiment is the post-reaction acquisition of pure heptane-dissolved catalyst resulting from the complete lack of solubility in heptane of the reaction product; under this scenario, product-catalyst separation is a simple result of product precipitation from solution. Indeed, many polar organic products of the inventive catalysis are not especially soluble in heptane and can be easily removed by decantation or filtration. These different routes (liquid/liquid or liquid/solid separation) of catalyst recycling afforded by the invention are more efficient than those strategies previously described (Ahmed et al., 1999; Connon et al., 2002; Garber et al., 2000; Jafarpour and Nolan, 2000; Kingsbury and Hoveyda, 2005; Nguyen and Grubbs, 1995; Yao and Zhang, 2004).

Figure 2:
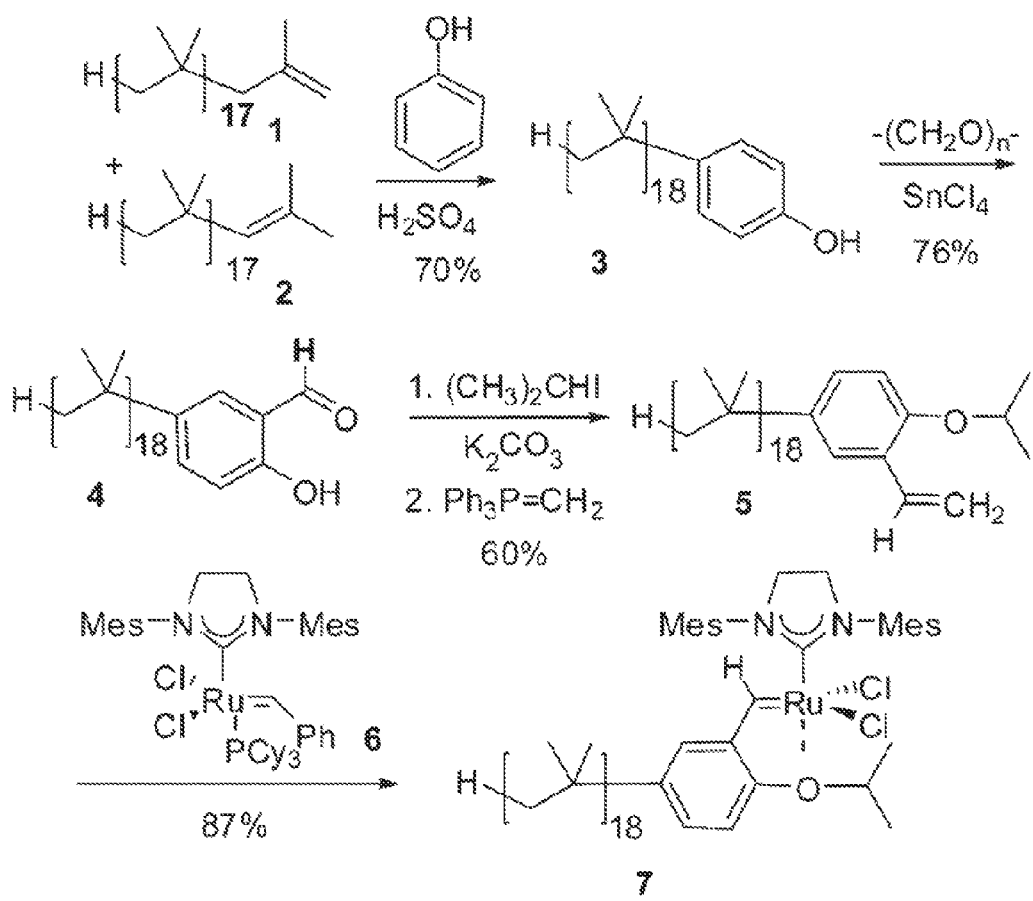
FIG. 2 shows a reaction scheme for the synthesis of a PIB-supported second-generation Hoveyda-Grubbs catalyst. The numbers shown in bold (1-7) refer to the different molecules involved in this process. Refer to Study 1.
Figure 3:
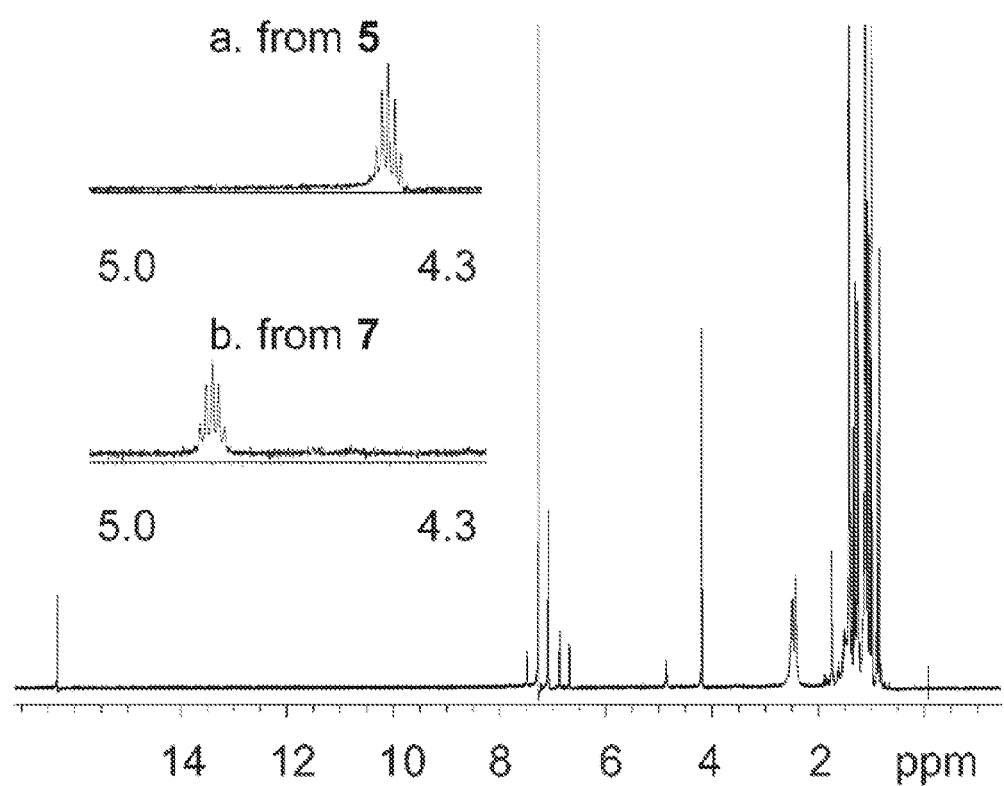
FIG. 3 shows the $^1$H NMR spectrum of a PIB-bound ruthenium metathesis catalyst 7 showing changes in the i-Pr heptet in insets a and b for 5 and 7, respectively. Molecules 5 and 7 are depicted in FIG. 2. Refer to Study 1.

Synthesis of PIB-Supported Grubbs-Hoveyda Second Generation Catalyst (For molecules 1-7 indicated in bold, refer to FIG. 2) The general strategy for synthesis of a heptane-soluble metathesis catalyst relied on the use of commercially available vinyl-terminated polyisobutylene (PIB). While this material can be >90%=CH2-terminated polyisobutylene 1, some samples contain as much as 20% of the internal double bond (e.g. polyisobutylene 2). A Friedel-Crafts alkylation of either structurally isomeric polyisobutylene oligomer, however, yields the same 4-(polyisobutyl)phenol product 3 (Li et al., 2005). Formylation of this oligomeric phenol by using paraformaldehyde produces the 2-hydroxy-5-(polyisobutyl)benzaldehyde 4. This product can in turn be converted into the oligomeric styrene derivative 5 by using a Wittig olefination. Exchange of the methylene group with the benzylidene group of the commercially available second-generation Grubbs catalyst 6 produced the desired heptane-soluble catalyst 7. The last step of this synthesis also used flash column chromatography to separate the PIB-bound Ru complex 7 from starting materials. Chromatography is not usually used in the synthesis of polymer-bound catalysts but is feasible for complex 7 just as it is feasible for PEG-bound or dendrimer-bound catalysts (Garber et al., 2000; Hong and Grubbs, 2006). As is the case for other terminally functionalized polymer-bound ligands/catalysts, all of the intermediates in these syntheses could be characterized by $^1$H NMR spectroscopy (Li et al., 2005; Dickerson et al., 2002; Bergbreiter et al., 1989). FIG. 3 illustrates the sort of $^1$H NMR spectra that can be obtained for species such as catalyst 7. This spectrum establishes that catalyst 7, in similar fashion to its low molecular weight analogue, involves the isopropyloxy group in the Ru coordination sphere as the heptet due to the CH of the isopropyloxy shifts from δ 4.51 in 5 to δ 4.87 in 7 (FIG. 3, compare insets a and b).

Ring-Closing Metathesis Reactions.

(For molecules 8-17 indicated in bold, refer to Table 1) Other than having a PIB-containing ligand rendering catalyst 7 heptane-soluble, this catalyst had normal reactivity, converting a variety of α,ω-dienes into cyclic olefins at room temperature (Table 1). Catalyst 7 could be recycled multiple times using several different protocols. One approach used for separating products such as 9 and 17 away from the catalyst was to carry out the ring-closing metathesis reaction in heptane as a solvent and to then extract the products with acetonitrile (Table 1). In such cases, the less dense heptane phase contained catalyst 7 and recycling simply involved addition of fresh substrate.

TABLE 1

Ring-closing metathesis reactions with catalyst 7[a].

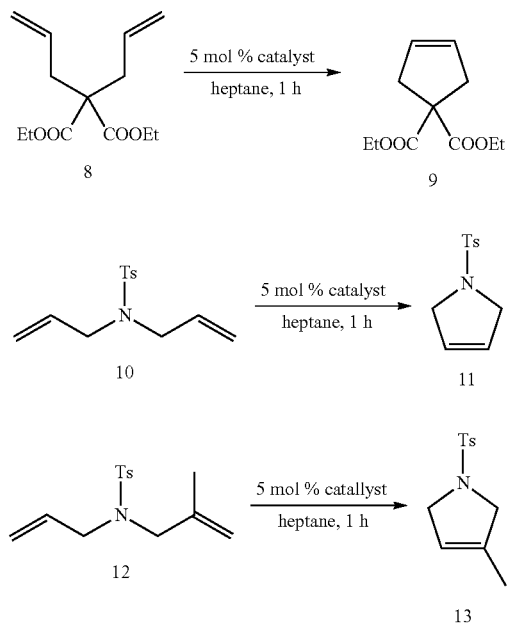
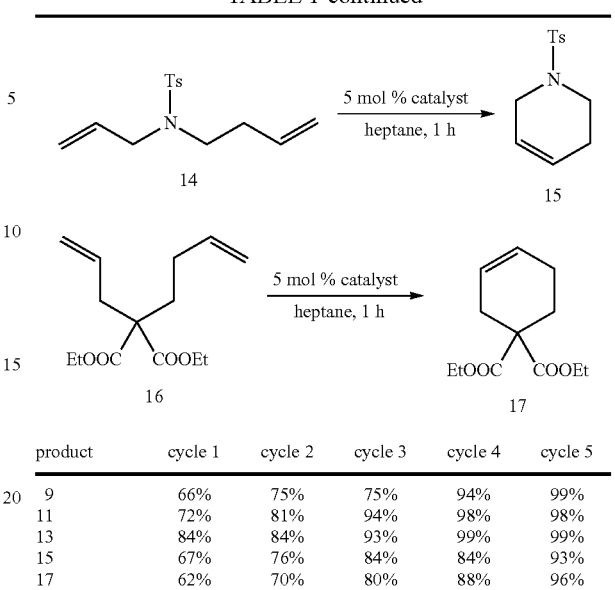

| product | cycle 1 | cycle 2 | cycle 3 | cycle 4 | cycle 5 |
|---------|---------|---------|---------|---------|---------|
| 9       | 66%     | 75%     | 75%     | 94%     | 99%     |
| 11      | 72%     | 81%     | 94%     | 98%     | 98%     |
| 13      | 84%     | 84%     | 93%     | 99%     | 99%     |
| 15      | 67%     | 76%     | 84%     | 84%     | 93%     |
| 17      | 62%     | 70%     | 80%     | 88%     | 96%     |

[a]Yields in cycles 1-5 are of products isolated by solvent removal.

While catalyst 7 was equivalent in reactivity to the commercially available catalyst 6, its solubility in heptane and the generally poor solvating ability of heptane toward many polar organic products makes another recycling scheme possible. For example, using substrates 10, 12 and 14 (Table 1), a reaction was carried out through at least five cycles by simply adding these heptane-soluble starting materials to the heptane solution of the catalyst. After one hour, the heterocyclic products precipitated from the heptane solvent leaving a solution of the catalyst that can be separated by forced siphon and reused. The apparent increases in yields from cycles 1-5 in Table 1 reflect saturation of the heptane phase by products (Bergbreiter and Li, 2004; Bergbreiter et al., 2001). If a catalyst were used through multiple cycles this would pose little problem unless the product or by-products were heptane-soluble (Bergbreiter et al., 2001).

The efficiency of separation of catalyst and product was evaluated by inductively coupled plasma-mass spectrometry (ICP-MS) analysis, using a sample of products 9 and 11 from the first and third reaction cycles of cyclization reactions as shown in Table 1. Combustion of product 9 and digestion of any residue in concentrated sulfuric acid showed the presence of about 20 ppm Ru in the product phase. This translates into recovery of about 97% of the Ru catalyst that is available for a second reaction cycle. The loss of Ru presumably reflects the fact that the present scheme requires the Ru-methylidene intermediate formed from 7 to be recaptured by 5 formed in situ for complete Ru recovery. Inefficiencies in this process and loss of Ru to another phase are most notable in the higher level of Ru contamination in the experiment where product 11 precipitated from heptane. In this case, about 96% of the Ru catalyst was still recovered, but the solid product contained about 1000 ppm of Ru. This high concentration of Ru is due to the small volume of the product phase and partitioning of Ru species onto the small volume of the polar solid that is formed. This observation suggests that designing other systems where the Ru species in the catalytic cycle always has a hydrocarbon soluble ligand may lower Ru leaching.

Ring-Opening Metathesis Reactions.

Figure 4:
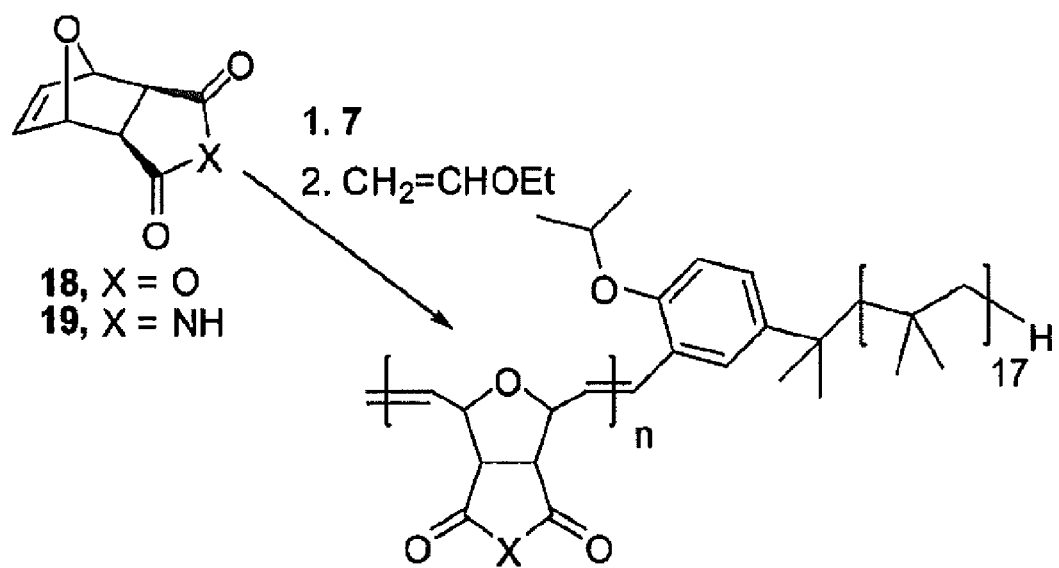
FIG. 4 shows a ring-opening metathesis polymerization (ROMP) reaction using catalyst 7. The numbers shown in bold (18 and 19) refer to the different substrates used in the ROMP reaction. Refer to Study 1.

(For molecules 18-19 indicated in bold, refer to FIG. 4) The reactivity of catalyst 7 was also tested in ring-opening metathesis polymerization (ROMP) reactions (Buchmeiser, 2000; Grubbs and Tuman, 1989). In this case, the use of catalyst 7 is expected to generate an amphiphilic block copolymer since the PIB chain of the ligand will be the end group of the product polymer chain. The ROMP reactions of substrates 18 and 19 with catalyst 7 were studied in tetrahydrofuran (THF) at room temperature (FIG. 4), using a monomer:initiator ratio of 30:1. $^1$H NMR showed quantitative conversion in both reactions after twenty minutes. The reactions were then quenched with ethyl vinyl ether, and the resulting polymers were isolated. Catalyst 7 is thus useful in ring-closing metathesis and ROMP chemistry.

In summary, the studies described above show that PIB oligomers constitute an excellent heptane-selectively soluble polymer support for a second-generation Hoveyda-Grubbs catalyst. The derivatization and chemistry of these oligomers can be easily monitored by conventional spectroscopy. The activity of the PIB-supported catalyst is analogous to that of other soluble polymer or non-supported catalysts.

Materials and Methods (Study 1)

General

The $^1$H NMR spectra were recorded on an Inova 500-MHz spectrometer operating at 499.95 MHz. $^{13}$C NMR spectra were recorded on an Inova 500-MHz spectrometer operating at 125.719 MHz. Chemical shifts were reported in parts per million (δ) relative to residual proton resonances in the deuterated chloroform (CDCl$_3$). Coupling constants (J values) were reported in hertz (Hz), and spin multiplicities are indicated by the following symbols: s (singlet), d (doublet), t (triplet), q (quartet), and m (multiplet). UV-Vis spectra were obtained using a Varian Cary 100 spectrometer. IR spectra were obtained using a Bruker Tensor 27 FT-IR. ICP-MS were obtained using a Perkin Elmer DRC II instrument.

All reactions were carried out under an inert atmosphere unless otherwise noted. Acetonitrile, heptane, dimethylformamide, ethanol, dichloromethane, and toluene were purchased from EMD Chemicals, Inc. and used as received. All other chemicals were purchased from Sigma-Aldrich and used as received. Products were isolated simply by evaporation of solvent without chromatography. The product spectra contain traces of alkane solvents, residual polyisobutylene, or water.

Synthesis of PIB-Supported Catalyst 4-(polyisobutyl)phenol

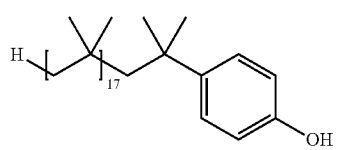

A mixture of 16.75 g (178 mmol) of phenol, 8.9 g (8.9 mmol) of polyisobutylene (Glissopal® 1000), and 1.05 g (10.7 mmol) of concentrated sulfuric acid in 200 mL of dichloromethane was stirred for 3 d at room temperature. The solvent was removed under reduced pressure and then 250 mL of hexanes was added to the viscous residue. The hexanes solution was washed first with 150 mL of dimethyl formamide three times and then with 150 mL of 90% ethanol/water three times. The hexane phase was dried over sodium sulfate. The solvent was removed under reduced pressure to yield a light yellow viscous residue. The yield of 4-(polyisobutyl) phenol was 70%. $^1$H NMR (500 MHz, CDCl$_3$), δ: 0.8-1.8 (m, 138H), 1.8 (s, 2H), 6.75 (d, J=8.79 Hz, 21H), and 7.23 (d, J=8.79 Hz, 2H). $^{13}$C NMR (125 MHz, CDCl$_3$), δ: 153.19, 142.99, 127.52, 114.75, multiple peaks between 58-60, 38-38.5, and 30.75-33.

2-hydroxy-5-(polyisobutyl)benzaldehyde

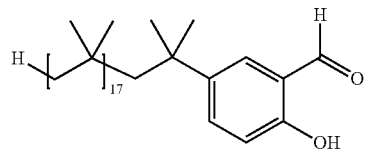

A mixture of 3.42 g (3.13 mmol) of 4-(polyisobutyl)phenol and 0.58 mL (5 mmol) of 2,6-lutidine in 40 in L of toluene was stirred under room temperature for 30 min. A solution of SnCl$_4$ (0.15 mL, 1.25 mmol) in 10 mL of toluene was added slowly to the reaction. The reaction was then stirred under room temperature for 1 h at which point 0.56 g (18.78 mmol) of paraformaldehyde was added to reaction. The reaction was heated for 12 h at 100° C. After the reaction mixture cooled to room temperature, it was acidified to pH 2.0 with 2M HCl. The organic layer was separated, the solvent was removed under reduced pressure, and then 250 mL of hexanes was added to the viscous residue. The hexanes solution was washed first with 150 mL of dimethyl formamide three times and then with 150 mL of 90% ethanol/water three times. The hexane phase was dried over sodium sulfate. The solvent was removed under reduced pressure to yield a light yellow viscous residue. The yield of 2-hydroxy-5-(polyisobutyl)benzaldehyde was 76%. $^1$H NMR (500 MHz, CDCl$_3$), δ: 0.8-1.8 (m, 155H), 1.8 (s, 2H), 6.94 (d, J=8.54 Hz, 1H), 7.48 (m, 1H), 7.57 (d, J=2.44, 8.54 Hz, 1H), 9.9 (s, 1H), and 10.88 (s, 1H). $^{13}$C NMR (125 MHz, CDCl$_3$), δ: 197.07, 159.65, 142.40, 135.74, 130.73, 120.21, 117.24, multiple peaks between 58-60, 38-38.5, and 30.75-33.

2-isoproproxy-5-(polyisobutyl)benzaldehyde

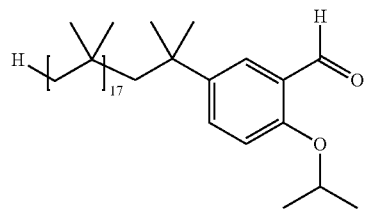

A mixture of 2.5 g (2.25 mmol) of 2-hydroxy-5-(polyisobutyl)benzaldehyde and 0.425 g (2.5 mmol) of isopropyl iodide in 10 mL of DMF and 10 mL of heptane was heated to 80° C. over night, then cooled to room temperature. At this point, 50 mL of hexanes was added to the solution. The hexanes solution was washed first with 30 mL of dimethyl formamide three times and then with 30 mL of 90% ethanol/water three times. The hexanes phase was dried over sodium sulfate. The solvent was removed under reduced pressure to yield the 2-isoproproxy-5-(polyisobutyl)benzaldehyde product as a light yellow viscous residue with 76% yield. $^1$H NMR (500 MHz, CDCl$_3$), δ: 0.8-1.8 (m, 168H), 1.8 (s, 2H), 4.66 (m, 1H), 6.92 (d, J=9.04 Hz, 1H), 7.53 (d, J=2.69, 8.79 Hz, 1H), 7.82 (d, J=2.69 Hz, 1H), and 10.49 (s, 1H). $^{13}$C NMR (125 MHz, CDCl$_3$), δ: 190.68, 158.75, 142.92, 134.06, 125.63, 125.21, 113.83, 71.34 multiple peaks between 58-60, 38-38.5, and 30.75-33.

1-isoproproxy-4-(polyisobutyl)-2-vinylbenzene

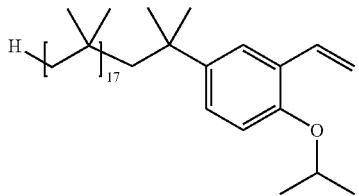

Methyltriphenylphosphonium iodide (3.21 g, 7.96 mmol) was added to 30 mL of THF. Then 5 mL of 1.6 M BuLi was added slowly to the solution. After 2 h stirring the solution turned bright yellow. The solution was cooled to −78° C. and a solution of 4.6 g (3.98 mmol) of 2-isoproproxy-5-(polyisobutyl)benzaldehyde ether in THF was added slowly to the mixture. The reaction was stirred overnight. The solvent was removed under reduced pressure and then 100 mL of hexanes was added to the viscous residue. The hexanes solution was washed first with 75 mL of dimethyl formamide three times and then with 75 mL of 90% ethanol/water three times. The hexanes phase was dried over sodium sulfate. The solvent was removed under reduced pressure to yield the 1-isoproproxy-4-(polyisobutyl)-2-vinylbenzene product as a light yellow viscous residue with 80% yield. $^1$H NMR (500 MHz, CDCl$_3$), δ: 0.8-1.8 (m, 168H), 1.8 (s, 2H), 4.51 (m, 1H), 5.73 (dd, J=1.71, 11.23 Hz, 1H), 5.73 (d, J=1.46, 17.82 Hz, 1H), 6.81 (d, J=8.54 Hz, 1H), 7.07 (dd, J=10.98, 17.82 Hz, 1H), 7.19 (dd, J=2.45, 8.55 Hz, 1H), and 7.46 (d, J=2.44 Hz 1H). $^{13}$C NMR (125 MHz, CDCl$_3$), δ: 153.13, 142.54, 132.96, 127.11, 126.71, 124.62, 113.98, 113.67, 71.11, multiple peaks between 58-60, 38-38.5, and 30.75-33.

PIB-Supported Grubbs-Hoveyda Second Generation Catalyst

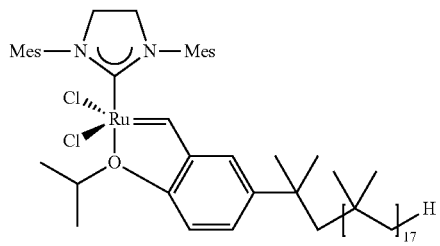

A mixture of 2 g (1.72 mmol) of 1-isoproproxy-4-(polyisobutyl)-2-vinylbenzene, 0.12 g (1.21 mmol) of CuCl, and 0.73 g (0.86 mmol) of the second generation Grubbs catalyst in dichloromethane was stirred at 40° C. overnight. The solution turned from red to green as the reaction progressed. The solvent was removed under reduced pressure and the residue was purified by column chromatography (2:1 hexane:dichloromethane) to yield a dark green viscous solution. The solvent was removed under reduced pressure resulting in dark green viscous residue of the PIB-supported catalyst product (87% yield). $^1$H NMR (500 MHz, CDCl$_3$), δ: 0.8-1.8 (m, 156H), 1.8 (s, 2H), 2.42-2.49 (m, 18H), 4.20 (s, 4H), 4.87 (m, 1H), 6.71 (d, J=8.7 Hz, 1H), 6.87 (d, J=1.83 Hz, 1H), 7.09 (s, 4H), 7.48 (dd, J=2.06, 9.15 Hz, 1H), and 16.32 (s, 1H). $^{13}$C NMR (125 MHz, CDCl$_3$), δ: 298.35 (m), 212.65, 150.40, 145.13, 145.11, 138.97, 129.58, 129.57, 129.55, 127.55, 120.59, 112.25, 74.81, multiple peaks between 58-60, 38-38.5, and 30.75-33. $\lambda_{max}$=591 nm. IR (KBr, br: broad, s: strong, m: medium, w: weak): 2954 (br), 2870 (br), 1729 (w), 1612 (w), 1592 (w), 1488 (s), 1455 (m), 1391 (s), 1367 (s), 1297 (m), 1267 (s), 1232 (s), 1139 (m), 1108 (m), 1037 (m), 927 (m), 854 (m), 815 (m), 739 (S), 704 (m), 649 (m), 621 (w), 580 (m).

Procedures and Product Characterization Data for Metathesis Reactions.

Conversion of substrate 8 to product 9 (Table 1):

A mixture of 120 mg (0.5 mmol) substrate 8 and 40 mg (0.025 mmol) of catalyst 7 were dissolved in 5 mL of heptane. The reaction was stirred for 1 h. Once the reaction was completed, 3 mL of acetonitrile was added to the reaction mixture and the biphasic mixture was stirred vigorously. After a gravity separation, the acetonitrile layer was removed. The solvent was removed from this phase under reduced pressure to yield compound 9 (Yao and Zhang, 2003). $^1$H NMR (500 MHz, CDCl3), δ: 1.24 (t, J=7.33 Hz, 6H), 3.0 (s, 4H), 4.19 (q, J=7.32 Hz, 4H), and 5.60 (m, 2H). $^{13}$C NMR (125 MHz, CDCl$_3$), δ: 172.49, 128.05, 61.76, 59.07, 41.08, and 14.27.

Conversion of Substrate 16 to Product 17 (Table 1):

A mixture of 127 mg (0.5 mmol) substrate 16 and 40 mg (0.025 mmol) of catalyst 7 were dissolved in 5 mL of heptane. The reaction was stirred for 1 hour. Once the reaction was completed, 3 mL of acetonitrile was added to the reaction mixture and stirred vigorously. After both phases of the solvent are separated, the acetonitrile layer was removed. The heptane layer was recycled in the subsequent reactions. The solvent was removed under reduced pressure to yield compound 17 (Romero et al., 2004). $^1$H NMR (500 MHz, CDCl$_3$), δ: 1.25 (m, 6H), 2.12 (m, 4H), 2.56 (s, 2H), 4.19 (m, 4H), and 5.68 (m, 2H). $^{13}$C NMR (125 MHz, CDCl$_3$), δ: 171.84, 126.31, 124.24, 61.49, 53.16, 30.64, 27.57, 22.54, and 14.27.

Conversion of Substrate 10 to Product 11 (Table 1):

In a second procedure, a ring-closing metathesis reaction was carried out where the product self-separated from the heptane solution of the catalyst. In this reaction, a mixture of 125 mg (0.5 mmol) of substrate 10 (Yao and Zhang, 2003) and 40 mg (0.025 mmol) of catalyst 7 were dissolved in 5 mL of heptane. The reaction was stirred for 1 h. As the reaction proceeded, product 11 precipitated out of solution; therefore it was separated from the reusable heptane solution of the catalyst and dried under reduced pressure. The heptane layer was directly recycled in subsequent reactions. $^1$H NMR (500 MHz, CDCl$_3$), δ: 2.44 (s, 3H), 4.13 (s, 4H), 5.66 (s, 2H), 7.33 (d, J=8.1 Hz, 2H), and 7.73 (d, J=8.3 Hz, 2H). $^{13}$C NMR (125 MHz, CDCl$_3$), δ: 143.68, 134.53, 130.0, 127.67, 125.70, 55.08, and 21.78. M.P. range=123.2-126.5° C.

Conversion of Substrate 12 to Product 13 (Table 1):

A second example of a self-separating product involved the diene substrate 12. A mixture of 125 mg (0.5 mmol) of the substrate 12 and 40 mg (0.025 mmol) of catalyst 7 were dissolved in 5 mL of heptane. The reaction was stirred for 1 h. As the reaction proceeded, product 13 precipitated out of solution. It was separated from the catalyst solution by filtration and dried under reduced pressure. The heptane layer was directly recycled in subsequent reactions. $^1$H NMR (500 MHz, CDCl$_3$), δ: 1.66 (s, 3H), 2.43 (s, 3H), 3.97 (m, 2H), 4.07 (m, 2H), 5.25 (m, 1H), 7.32 (d, J=8.1 Hz, 2H), and 7.72 (d, J=8.2 Hz, 2H). $^{13}$C NMR (125 MHz, CDCl$_3$), δ: 143.58, 135.31, 129.97, 127.70, 11932, 117.84, 57.92, 55.37, 21.78, and 14.32. M.P. range=100.8-101.8° C.

Conversion of Substrate 14 to Product 15 (Table 1):

A mixture of 125 mg (0.5 mmol) substrate 14 and 40 mg (0.025 mmol) of catalyst 7 were dissolved in 5 mL of heptane. The reaction was stirred for 1 h. As the reaction proceeded, product 15 precipitated out of solution. After 1 h, the product was separated from the heptane solution of the catalysts by filtration. The heptane catalyst solution was directly recycled in subsequent reactions. The product was dried and characterized. $^1$H NMR (500 MHz, CDCl$_3$), δ: 2.24 (m, 2H), 2.45 (s, 3H), 3.19 (t, J=5.61 Hz, 2H), 3.59 (m, 2H), 5.63 (m, 1H), 5.77 (m, 1H), 7.34 (d, J=8.06 Hz, 2H), and 7.70 (d, J=8.3 Hz, 2H). $^{13}$C NMR (125 MHz, CDCl$_3$), δ: 143.73, 133.62, 129.86, 127.95, 125.31, 123.0, 45.02, 42.88, 25.51, and 21.77. M.P. range=99.7-102.2° C.

Ring-Opening of Substrates 18 and 19 (FIG. 4):

Catalyst 7 (20 mg, 0.012 mmol) was dissolved in 2 mL of THF. It was then added dropwise to a THF solution (5 mL) of the substrate monomer (18: 60.9 mg, 0.37 mmol, 30 equiv.; 19: 60.5 mg, 0.37 mmol, 30 equiv.) and the reaction was stirred at room temperature. The color of the solution turned from green to light gray in less than 2 min. The solution was stirred for an additional 20 min, then ethyl vinyl ether (0.4 mL, 600 equiv.) was added and stirring continued for 15 min. The polymerization solution was then poured into methanol (100 mL) while stirring to give a light greenish solid that was collected and dried under vacuum.

Ruthenium Analysis Procedure:

The sample that was to be analyzed (20-30 mg) was added to a 20 mL vial along with 4 g of concentrated nitric acid. The mixture was heated to 120° C. until everything dissolved. At this point 4 g of concentrated sulfuric acid was added to the solution. The solution was then allowed to stand at room temperature for 24 h. At this point, the concentrated acidic aqueous solution was transferred to a 50-mL plastic bottle and diluted to 50 mL with 1% nitric acid solution. A portion (0.2063 g) of the solution was further diluted to 50 mL with an additional portion of 1% nitric acid. Then, the diluted sample solution was analyzed by ICP-MS.

Study 2

Polyisobutylene (PIB) Phase-Anchored N-heterocyclic carbene Ligands.

Molecules 2-23 as discussed in the below text for this study refer to certain molecules shown throughout the Materials and methods (Study 2) section and Table 2. These numbers do not refer back to the molecules described in Study 1.

N-Heterocyclic carbenes (NHC) have become widely used ligands for organometallic chemistry since Arduengo's initial reports (Arduengo et al., 1991). While their use in metathesis chemistry is most common, metal complexes derived from these structurally diverse ligands are useful in many catalytic processes (Liddle et al., 2007; Glorius, 2007). N-Heterocyclic carbenes themselves are useful organocatalysts too (Marion et al., 2007). Thus, there is significant interest in strategies that facilitate separation, recovery and reuse of these ligands and their metal complexes. Below are described new routes to recoverable, heptane-soluble NHC ligands and their use as supports for recoverable, reusable metathesis catalysts.

Insoluble cross-linked polymers or inorganic supports for recoverable reusable NHC-ligated metal complexes useful in catalysis are known (Clavier et al., 2007). Examples of soluble polymer supports for these catalysts have also been described, but these latter reports are limited to the use of poly(ethylene glycol) (PEG) supports (Hong and Grubbs, 2006; Zeitler and Mager, 2006). PEG supports attached to an imidazolium carbon or to an imidazolium nitrogen yield NHC catalysts that are water-soluble or recoverable by solvent precipitation. Described in this example is the use of heptane-soluble polyisobutylene (PIB) phase anchors (Li et al., 2005) to prepare separable NHC metal complexes. As shown below, PIB groups can be attached to these carbene precursors and the product PIB-bound NHCs form metal complexes that are phase selectively soluble in the heptane phase of thermomorphic mixtures of heptane and polar solvents. Alternatively heptane solutions of these NHCs can be extracted with polar solvents with minimal losses of the metal complex. This behavior is demonstrated both for Ag(I) complexes and with separable, recoverable, and reusable Ru catalysts useful in ring closing metatheses.

Three approaches were explored to synthesize PIB-supported NHC ligands. First, a Friedel-Crafts alkylation of a commercially available mixture of alkene-terminated PIBs afforded 2,6-dimethyl-4-(polyisobutyl)aniline (molecule 2) which, like mesityl amine, reacts with oxalyl chloride to form the diamide (molecule 3). This reaction used excess 2 which was separated using an Amberlyst resin as a scavenger (Liu et al., 1998). The diamide product was then reduced to form a diamine that was converted into the PIB-bound imidazolium tetraborofluorate salt (molecule 4) using known chemistry (Hong and Grubbs, 2006).

A second route to PIB-bound NHC ligands that has also been used by Zeitler's group to synthesize PEG-bound NHCs uses a 'Click' cycloaddition of a mono- or di-propargylic imidazole derivative with a soluble polymeric azide (Zeitler and Mager, 2007; Wu and Fokin, 2007).

Formation of metal complexes from the imidazolium salts used either KHMDS to deprotonate 4 to synthesize a PIB-supported Hoveyda-Grubbs second generation catalyst (molecule 8) from the Hoveyda-Grubbs first generation catalyst 7 (Hong and Grubbs, 2006) or used Ag$_2$O (Wang and Lin, 1998) to react with 6 or 9 to prepare the Ag(I) complexes (molecules 10 and 11).

These metal complexes were characterized by solution-state $^1$H and $^{13}$C NMR spectroscopy. Both the PIB-bound pincer compound 10 and compound 11 had spectra that were like those of low molecular weight pincer Ag(I) complexes formed using octadecylazide in place of the PIB azide. In the case of 11, the carbene carbon also exhibited C—Ag coupling. An analysis for Ag showed that 10 or 11 contained 4.06% or 3.51% Ag (4.05% or 3.89% Ag was expected for 10 or 11 if the PIB groups in the product have a degree of polymerization of 20). ICP-MS analyses showed that the Ag(I) complex 10 had 98:2, 99:1, or 96:4 selective solubility in heptane in mixtures of heptane with CH$_3$CN, AcOCH$_2$CH$_2$OAc, or DMF. Complex 11 had a 98:2 phase selective solubility in a partially thermomorphic heptane/CH$_3$CN mixture. The phase selective solubility of 11 in the heptane phase of an equivolume heptane/CH$_3$CN mixture was completely different than that of the lower molecular weight analog (molecule 12). ICP-MS showed the heptane phase selective solubility for 12 was <1:1000, which represents a >1000-fold difference.

Studies of the phase selective solubility of the Ru complex 8 and its lower molecular weight analog (molecule 13) mirrored those for the Ag complexes. A UV-vis analysis showed a 1000-fold difference of 99:1 vs 1:100 heptane phase selective solubility when 8 or 13 was present in a thermomorphic equivolume mixture of heptane and CH$_3$CN. These UV-visible spectroscopy results are apparent in a visual inspection (FIG. 9a-c) of the reactions and were confirmed by ICP-MS analyses that showed a 97:3 versus a 1:99 phase selective solubility for 8 and 13 in the heptane phase of a heptane/CH$_3$CN mixture.

Ru catalytic complexes such as 8 are structurally analogous to the Ru complex 13 already used in ring-closing metathesis (Garber et al., 2000). However, unlike 13, 8 could be recycled in up to twenty reaction cycles to convert a variety of 1,6-dienes and 1,7-dienes into cyclic olefins at room temperature (Table 2). Recycling of catalyst 8 was accomplished in one of two ways. The first approach for performing ring-closing metathesis of dienes 14 and 22 (Table 2) employed heptane as a solvent, afterwhich product was extracted with $CH_3CN$. In this approach, the less dense heptane phase containing catalyst 8 was reused by simply adding fresh substrate. Products 15 and 23 (Table 2) were then isolated by removal of the $CH_3CN$.

TABLE 2

Ring-closing metathesis reactions with catalyst 8[a].

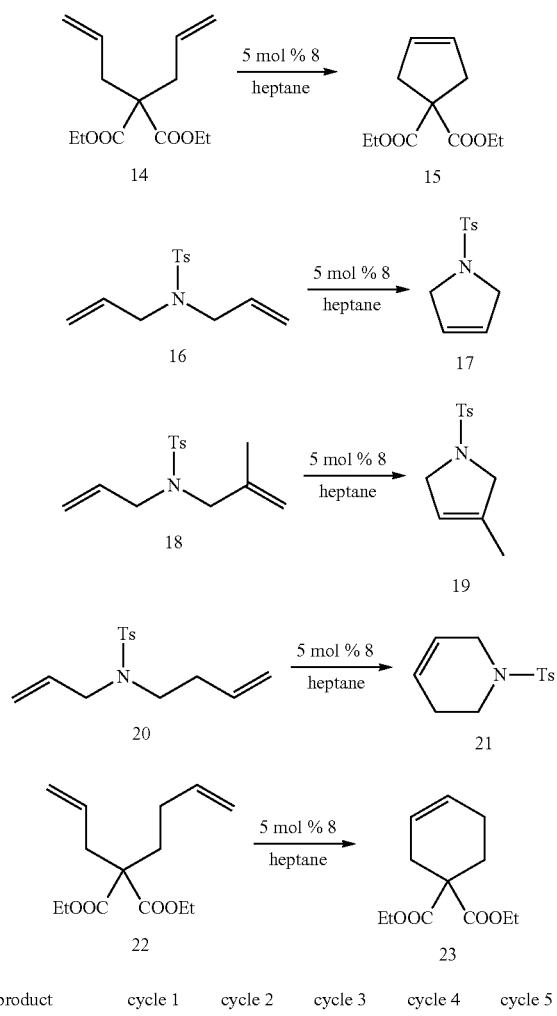

| product | cycle 1 | cycle 2 | cycle 3 | cycle 4 | cycle 5 |
|---------|---------|---------|---------|---------|---------|
| 15 | 60% | 75% | 85% | 94% | 94% |
| 17[b] | 72% | 81% | 99% | 99% | 98% |
| 19 | 67% | 75% | 93% | 99% | 99% |
| 21 | 59% | 76% | 84% | 93% | 93% |
| 23 | 62% | 71% | 97% | 99% | 99% |

[a]Yields in cycles 1-5 are for isolated products in 0.5 mmol scale reactions and increase cycle to cycle because of saturation of the catalyst-containing heptane phase by reaction products.
[b]20 cycles (average yield of 97% per cycle) were carried out with reaction times of two hours in the 12th-13th cycles, four hours in 14th-18th cycles, and eight hours in 19th-20th cycles.

While most catalyst recovery schemes focus on catalyst separation, the solubility of catalyst 8 in heptane and the low solubility of many organic compounds in heptane allowed the use of another recycling scheme for substrates 16, 18, and 20 (Table 2). In these cases, starting materials were soluble in a heptane solution containing catalyst 8; however, the products resulting from catalysis precipitated from solution, thereby effectively separating themselves from the catalyst. In these cases, products 17, 19, and 21 (Table 2) were recovered by simple filtration; recycling of the catalyst only required adding a fresh heptane solution of substrate to the recovered solution containing 8.

The recyclability/recoverability of catalyst 8 was evaluated by ICP-MS analysis. Samples of product 17 (Table 2) from the first, second, fifth, and fourteenth reaction cycles were digested in concentrated nitric acid and then in sulfuric acid. The ICP-MS results showed that only 0.28-0.54% of the starting Ru was in the product phase. This level of leaching of Ru from the catalyst phase is comparable to that seen for a water-soluble PEG-supported SIMes (Hong and Grubbs, 2007). Moreover, the metal leaching is approximately 10-fold less than that observed for the Ru catalyst that incorporated a PIB-bound benzylidene ligand (described in Study 1; Hongfa et al., 2007).

Materials and Methods Study 2)

General

The $^1$H-NMR spectra were recorded on an Inova 500 MHz and 300 MHz spectrometer operating at 499.95 MHz and 299.916 MHz, respectively. $^{13}$C-NMR spectra were recorded on an Inova 500 MHz spectrometer operating at 125.719 MHz. Chemical shifts were reported in parts per million (δ) relative to residual proton resonances in the deuterated chloroform ($CDCl_3$). Coupling constants (J values) were reported in hertz (Hz), and spin multiplicities are indicated by the following symbols: s (singlet), d (doublet), dd (doublet of doublet), t (triplet), q (quartet), b (broad), and m (multiplet). UV-Vis spectra were obtained using Agilent 8453 UV-Visible spectrometer. ICP-MS data were obtained using a Perkin Elmer DRC II instrument.

All reactions were carried out under an inert atmosphere unless otherwise noted. Acetonitrile, heptane, dimethylformamide, ethanol, dichloromethane, tetrahydrofuran, and toluene were purchased from EMD and used as received. Polyisobutylene was obtained from BASF. All other chemicals were obtained from Sigma-Aldrich and used as received.

Synthesis of PIB-Supported NHC, Grubbs-Hoveyda 2nd Generation Catalyst, and Ag(I) Complexes 2,6-Dimethyl-4-(polyisobutyl)aniline (molecule 2)

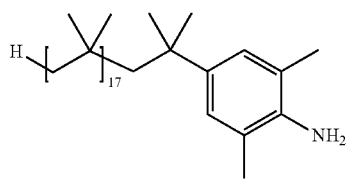

A mixture of 12.4 g (102 mmol) of 2,6-dimethylaniline, 10.15 g (10.15 mmol) of polyisobutylene (Glissopal® 1000), and 4.4 g (33 mmol) of aluminum trichloride was stirred for 3 d at 200° C. in a pressure vessel. After 3 d, the deep purple solution reaction was cooled to approximately 100° C. and added to 200 mL of hexane. The solution so formed was washed with 150 mL of dimethylformamide three times and then with 150 mL of 90% ethanol/water three times. After drying over sodium sulfate, the solvent was removed under reduced pressure and the product was purified by column chromatography (eluted first with hexane and then with dichloromethane). Solvent removal afforded the product as a light yellow viscous residue. The yield was 65% (7.39 g). $^1$H-NMR (500 MHz, CDCl$_3$), δ: 0.8-1.6 (m, 140H), 1.8 (s, 2H), 2.19 (s, 6H), 3.45 (s, 2H), and 6.92 (s, 2H). $^{13}$C-NMR (125 MHz, CDCl$_3$), δ: 18.26, multiple peaks between 30-40 and 58-60, 121.28, 126.30, 140.06, and 140.27.

N,N'-Bis(2,6-dimethyl-4-(polyisobutyl)phenyl)oxalamide (molecule 3)

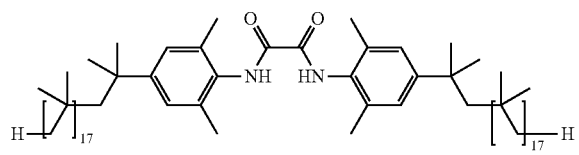

A mixture of 6 g (5.35 mmol) of 2,6-dimethyl-4-(polyisobutyl)aniline and 0.64 g (6.3 mmol) of triethylamine in 30 mL of dichloromethane was cooled to 0° C. A solution of oxalyl chloride (0.4 g, 3.15 mmol) in 5 mL of dichloromethane was added slowly to the reaction. The reaction was then stirred overnight. The solvent was removed under reduced pressure and added to 150 mL of hexane. The hexane solution was washed with 100 mL of 90% ethanol/water three times. The hexane phase was dried over sodium sulfate and shaken with 6 g of acid Amberlyst XN-1010 for 4 h, and then the resin was removed by filtration. The solvent was removed under reduced pressure to yield a light yellow viscous residue. The yield was 88% (5.40 g). $^1$H-NMR (500 MHz, CDCl$_3$), δ: 0.8-1.6 (m, 280H), 1.82 (s, 2H), 2.28 (s, 12H), 7.11 (s, 2H), and 8.82 (s, 2H). $^{13}$C-NMR (125 MHz, CDCl$_3$), δ: 18.26, multiple peaks between 30-40 and 58-60, 126.20, 129.30, 134.05, 150.15, and 158.25.

N,N'-Bis(2,6-dimethyl-4-(polyisobutyl)phenyl) ethane-1,2-diamine

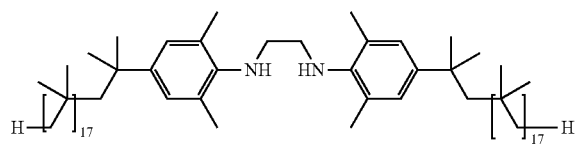

6.34 g (2.76 mmol) of N,N'-bis(2,6-dimethyl-4-(polyisobutyl)phenyl)oxalamide was dissolved in 30 mL of toluene, then 1.83 mL (18.67 mmol) of BH$_3$—SMe$_2$ was added to the solution. The solution turned from yellow to almost colorless. The reaction was heated at 90° C. overnight. The solvent was removed under reduced pressure and purified by column chromatography (10:1/hexane:dichloromethane). Solvent removal afforded a light yellow viscous residue. The yield was 61% (3.82 g). $^1$H-NMR (500 MHz, CDCl$_3$), δ: 0.8-1.6 (m, 280H), 1.77 (s, 2H), 2.30 (s, 12H), 3.17 (s, 4H), and 6.97 (s, 4H). $^{13}$C-NMR (125 MHz, CDCl$_3$), δ: 18.26, multiple peaks between 30-40 and 58-60, 49.30, 126.96, 128.92, 143.23, and 144.18.

N,N'-(Ethane-1,2-diylidene)bis(2,6-dimethyl-4-(polyisobutyl)aniline)

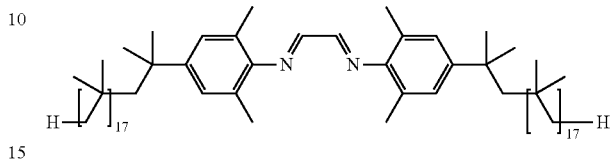

A mixture of 3.85 g (3.43 mmol) of 2,6-dimethyl-4-(polyisobutyl)aniline, and a catalytic amount of formic acid in 13 mL of hexane was prepared. A solution of 0.25 g (1.72 mmol) of glyoxal (40% in water) in 4 mL of isopropanol was then added to this solution. The reaction mixture initially turned cloudy for roughly 5 min and then became a clear yellow solution. The reaction was allowed to stir overnight. The solution was dried with sodium sulfate and the solvent was removed under reduced pressure to yield a dark yellow/brownish viscous residue. The yield was 94% (3.65 g). $^1$H-NMR (500 MHz, CDCl$_3$), δ: 0.8-1.6 (m, 280H), 1.77 (s, 2H), 2.20 (s, 12H), 7.06 (s, 4H), and 8.12 (s, 2H). $^{13}$C-NMR (125 MHz, CDCl$_3$), δ: 18.90, multiple peaks between 30-40 and 58-60, 126.06, 126.46, 128.50, 147.10, and 163.68.

1,3-Bis(2,6-dimethyl-4-(polyisobutyl)phenyl)imidazolium chloride

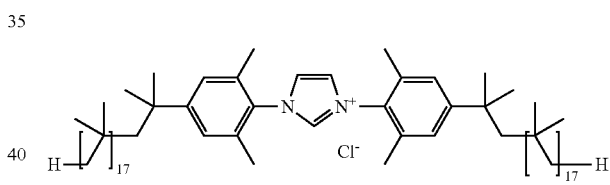

0.55 g (0.24 mmol) of N,N'-(ethane-1,2-diylidene)bis(2,6-dimethyl-4-(polyisobutyl)aniline) was dissolved in 2 mL of THF and 23 mg (0.24 mmol) of chloromethyl ethyl ether was added and heated to 40° C. overnight. The solvent was removed tinder reduced pressure and the residue was purified by column chromatography (dichloromethane). Solvent removal afforded a light brown viscous residue. The yield was 65% (0.36 g). $^1$H-NMR (500 MHz, CDCl$_3$), δ: 0.8-1.6 (m, 280H), 1.82 (s, 2H), 2.20 (s, 12H), 7.19 (s, 4H), 7.79 (s, 2H), and 10.21 (s, 1H). $^{13}$C-NMR (125 MHz, CDCl$_3$), δ: 18.90, multiple peaks between 30-40 and 58-60, 125.36, 127.44, 130.51, 133.57, 139.20, and 154.63.

1,3-Bis(2,6-dimethyl-4-(polyisobutyl)phenyl)-4,5-dihydro-imidazolium tetrafluoroborate (molecule 4)

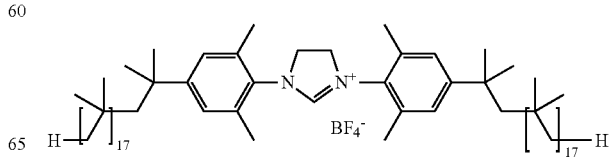

3.62 g (1.6 mmol) of N,N'-bis(2,6-dimethyl-4-(polyisobutyl)phenyl)ethane-1,2-diamine was dissolved in 10 mL of triethyl orthoformate and followed by the addition of 230 mg (2.19 mmol) of ammonium tetrafluoroborate and heated to 110° C. overnight. The solvent was removed under reduced pressure and purified by column chromatography (9:1/dichloromethane:methanol) resulted in a dark yellow viscous residue. The yield was 79% (2.99 g). $^1$H-NMR (500 MHz, CDCl$_3$), δ: 0.8-1.6 (m, 280H), 1.85 (s, 2H), 2.42 (s, 12H), 4.65 (s, 4H), 7.17 (s, 4H), and 7.65 (s, 1H). $^{13}$C-NMR (125 MHz, CDCl$_3$), δ: 18.36, multiple peaks between 30-40 and 58-60, 52.37, 127.60, 129.84, 134.54, 154.11, and 158.25.

1,3-Bis-((1-polyisobutyl-1H-1,2,3-triazol-4-yl)methyl)imidazolium bromide (molecule 6)

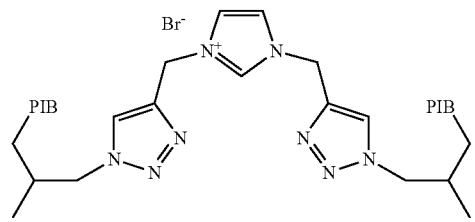

0.606 g (2.69 mmol) of 1,3-di-(prop-2-ynyl)imidazolium bromide (molecule 5), 17 mg (0.17 mmol) of CuCl, and 6.17 g (5.92 mmol) of azide-terminated polyisobutylene were dissolved in 105 mL of dichloromethane and 20 mL of methanol. The solution was stirred at room temperature for 24 h. After the reaction was completed, 1.19 g of EDTA and 20 mL of water was added and stirred at room temperature for 24 h. Dichloromethane layer was separated and remove under reduced pressure, and dissolved in 100 mL of hexane and washed with methanol until the methanol layer became colorless. The hexane was removed under reduced pressure. After the purification by column chromatography (eluted first with and then with 9:1/dichloromethane:methanol), the product was an orange vicious residue. The yield was 82% (5.12 g). $^1$H-NMR (500 MHz, CDCl$_3$), δ: 0.6-1.7 (m, 280H), 2.13 (m, 2H), 4.031 (dd, J=6, 13.5 Hz, 2H), 4.22 (dd, J=7.4, 13.5 Hz, 2H), 5.61 (s, 4H), 7.44 (s, 2H), 8.21 (s, 2H), and 10.85 (b, 1H) $^{13}$C-NMR (125 MHz, CDCl$_3$), δ: 20.55, multiple peaks between 28-39 and 57-60, 123.07, 125.59, 136.64, and 139.64.

1,3-Bis-((1-polyisobutyl-1H-1,2,3-triazol-4-yl)methyl)imidazol-2-ylidene-silver(I) bromide (molecule 10)

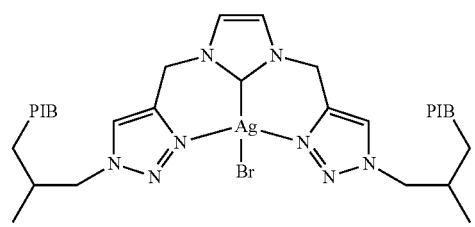

0.32 g (0.138 mmol) of 1,3-bis-((1-polyisobutyl-1H-1,2,3-triazol-4-yl)methyl)imidazolium bromide and 17.4 mg (0.075 mmol) of Ag$_2$O were dissolved in 3 mL of dichloromethane. The solution was stirred at 49° C. for 24 h. The solution was filtered to remove excess silver oxide and the solid was washed with dichloromethane. The solution was dried with sodium sulfate and solvents were removed under reduced pressure to yield an orange viscous residue. The yield was 93% (0.313 g). $^1$H-NMR (300 MHz, CDCl$_3$), δ: 0.6-1.8 (m, 280H), 2.10 (m, 2H), 4.02 (dd, J=6, 13.5 Hz, 2H), 4.21 (dd, J=7.4, 13.5 Hz, 2H), 5.30 (s, 4H), 7.22 (s, 2H), and 7.68 (s, 2H). $^{13}$C-NMR (125 MHz, CDCl$_3$), δ: 20.68, multiple peaks between 28-39 and 57-60, 121.55, 123.90, 142.14, and 181.16.

1,3-Bis-((1-octadecyl-1H-1,2,3-triazol-4-yl)methyl)imidazol-2-ylidene-silver(I) bromide

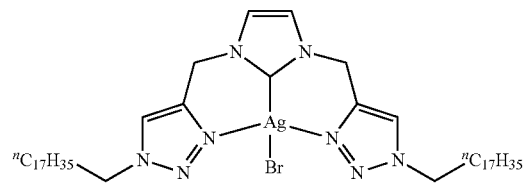

158.4 mg (0.194 mmol) of 1,3-bis-((1-octadecyl-1H-1,2,3-triazol-4-yl)ethyl)imidazolium bromide and 33.8 mg (0.146 mmol) of Ag$_2$O were dissolved in 10 mL of dichloromethane. The solution was stirred at 49° C. for 24 h. The solution was filtered through celite to remove excess silver oxide and the solid was washed with dichloromethane. The solution was dried with sodium sulfate and solvents were removed under reduced pressure to yield an orange viscous residue. The yield was 94% (0.1688 g). $^1$H-NMR (300 MHz, CDCl$_3$): 0.85 (t, J=6.6 Hz, 2H), 1.11-1.35 (m, 60H), 1.866 (m, 4H), 4.299 (t, J=7.5 Hz, 4H), 5.365 (s, 4H), 7.216 (s, 2H), 7.794 (s, 2H). $^{13}$C-NMR (CDCl$_3$): 14.10, 22.66, 26.48, multiple peaks between 28-31, 31.89, 46.69, 50.55, 121.58, 123.40, 14243, 181.67. FIRMS (ESI): Calc. for [M-Br]$^+$ ($^{107}$Ag isotope); 841.5713. Found: 841.6153.

1,3-Bis-(2,6-dimethyl-4-(polyisobutyl)phenyl)imidazol-2-ylidene-silver(I) chloride (molecule 11)

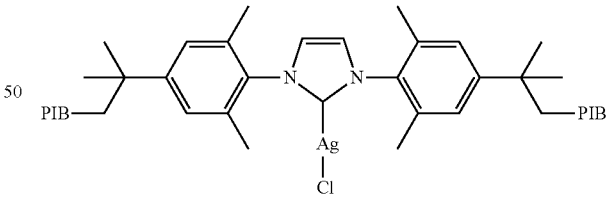

0.4268 g (0.185 mmol) of 1,3-bis(2,6-dimethyl-4-(polyisobutyl)phenyl)imidazolium chloride (molecule 9) and 30.8 mg (0.133 mmol) of Ag$_2$O were dissolved in 4 mL of dichloromethane. The reaction was refluxed for 16 h. After the reaction was cooled to room temperature, it was filtered through celite to remove excess Ag$_2$O. The solution was centrifuged at 5° C. to separate the finer silver salt. Solvent was removed under reduced pressure to yield an orange residue. The yield was quantitative (0.4667 g). $^1$H-NMR (300 MHz, CDCl$_3$), δ: 0.7-1.9 (m, 280H), 2.09 (s, 12H), 7.09 (s, 2H), and 7.15 (s, 4H). $^{13}$C NMR (125 MHz, CDCl$_3$), δ: 18.36, multiple peaks between 30-40 and 57-61, 122.68, 126.71, 133.76, 134.92, 152.39, and 182.875 (dd, J($^{13}$C-$^{107}$Ag)=236.6 Hz, J($^{13}$C-$^{107}$Ag)=271.6 Hz).

PIB-Supported Grubbs-Hoveyda 2nd Generation Catalyst (Molecule 8)

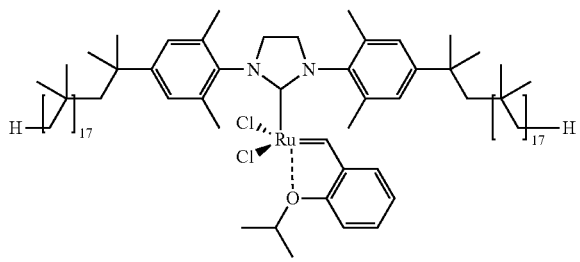

A mixture of 1.14 g (0.48 mmol) of 1,3-bis(2,6-dimethyl-4-(polyisobutyl)phenyl)-4,5-dihydro-imidazolium tetrafluoroborate, 0.15 g (0.75 mmol) of KHMDS, 0.05 g (0.5 mmol) of CuCl and 0.36 g (0.57 mmol) of $1^{st}$ generation Hoveyda-Grubbs catalyst (molecule 7) was prepared was dissolved in 5 mL of toluene. The solution was heated to 100° C. for 3 hours. Solvent was removed under reduced pressure and purified by column chromatography (dichloromethane) resulting in a dark green viscous residue. The yield was 60% (0.75 g). $^1$H-NMR (500 MHz, CDCl$_3$), δ: 0.8-1.6 (m, 280H), 1.87 (s, 2H), 2.41 (b, 6H), 2.62 (b, 6H) 4.15 (s, 4H), 4.90 (m, 1H) 6.8 (m, 2H), 6.98 (m, 1 μl), 7.22 (b, 4H), 7.47 (m, 1H), and 16.67 (s, 1H). $^{13}$C NMR (125 MHz, CDCl$_3$), δ: 21.62, multiple peaks between 30-40 and 58-60, 113.10, 122.42, 123.09, 126.53, 127.01, 129.69, 137.30, 139.21, 145.41, 145.44, 152.16, 152.43, 152.45, 211.19, and 297.23 (m).

Procedures for Ring Closing Metathesis Reaction

Conversion of Molecule 14 to Molecule 15 (Table 2):

120 mg (0.5 mmol) of substrate 14 and 65 nm g (0.025 mmol) of catalyst 8 were dissolved in 5 m L of heptane. After 1 h, the reaction was complete. At this point, 3 mL of acetonitrile was added to the reaction mixture. After vigorous stirring, the mixture was allowed to settle and the two phases were separated. The acetonitrile layer containing the product was dried under reduced pressure to yield compound 15. $^1$H-NMR (500 MHz, CDCl$_3$), δ: 1.24 (t, J=7.33 Hz, 6H), 3.0 (s, 4H), 4.19 (q, J=7.32 Hz, 4H), and 5.60 (m, 2H). $^{13}$C-NMR (125 MHz, CDCl$_3$), δ: 172.49, 128.05, 61.76, 59.07, 41.08, and 14.27.

Conversion of Molecule 16 to Molecule 17 (Table 2):

125 mg (0.5 mmol) of substrate 16 and 65 nm g (0.025 mmol) of catalyst 8 were dissolved in 5 m L of heptane. The reaction was stirred for 1 h during which time the product 17 precipitated from solution. The catalyst solution was separated from the product precipitates by filtration for reuse in a subsequent reaction cycle. The isolated solid product was dried under reduced pressure. $^1$H-NMR (500 MHz, CDCl$_3$), δ: 2.44 (s, 3H), 4.13 (s, 4H), 5.66 (s, 2H), 7.33 (d, J=8.1 Hz, 2H), and 7.73 (d, J=8.3 Hz, 2H). $^{13}$C-NMR (125 MHz, CDCl$_3$), δ: 143.68, 134.53, 130.0, 127.67, 125.70, 55.08, and 21.78. M.P. range=123.2-126.5° C.

Conversion of Molecule 18 to Molecule 19 (Table 2):

132 mg (0.5 mmol) of substrate 18 and 65 mg (0.025 mmol) of catalyst 8 were dissolved in 5 mL of heptane. The reaction was stirred for 1 h during which time the product 19 precipitated from solution. The catalyst solution was separated from the product precipitates by filtration for reuse in a subsequent reaction cycle. The isolated solid product was dried under reduced pressure. $^1$H-NMR (500 MHz, CDCl$_3$), δ: 1.66 (s, 3H), 2.43 (s, 3H), 3.97 (m, 2H), 4.07 (m, 2H), 5.25 (m, 1H), 7.32 (d, J=8.1 Hz, 2H), and 7.72 (d, J=8.2 Hz, 2H). $^{13}$C-NMR (125 MHz, CDCl$_3$), δ: 143.58, 135.31, 129.97, 127.70, 119.32, 117.84, 57.92, 55.37, 21.78, and 14.32. M.P. range=100.8-101.8° C.

Conversion of Molecule 20 to Molecule 21 (Table 2):

132 mg (0.5 mmol) of substrate 20 and 65 nm g (0.025 mmol) of catalyst 8 were dissolved in 5 mL of heptane. The reaction was stirred for 1 h during which time the product 21 precipitated from solution. The catalyst solution was separated from the product precipitates by filtration for reuse in a subsequent reaction cycle. The isolated solid product was dried under reduced pressure. $^1$H-NMR (500 MHz, CDCl$_3$), δ: 2.24 (m, 2H), 2.45 (s, 3H), 3.19 (t, J=5.61 Hz, 2H), 3.59 (m, 2H), 5.63 (m, 1H), 5.77 (m, 1H), 7.34 (d, J=8.06 Hz, 2H), and 7.70 (d, J=8.3 Hz, 2H). $^{13}$C-NMR (125 MHz, CDCl$_3$), δ: 143.73, 133.62, 129.86, 127.95, 125.31, 123.0, 45.02, 42.88, 25.51, and 21.77. M.P. range=99.7-102.2° C.

Conversion of Molecule 22 to Molecule 23 (Table 2):

127 mg (0.5 mmol) of substrate 22 and 65 mg (0.025 mmol) of catalyst 8 were dissolved in 5 mL of heptane. After 1 h, the reaction was complete. At this point, 3 mL of acetonitrile was added to the reaction mixture. After vigorous stirring, the mixture was allowed to settle and the two phases were separated. The acetonitrile layer containing the product was dried under reduced pressure to yield compound 23. $^1$H-NMR (500 MHz, CDCl$_3$), δ: 1.25 (t, J=7.08 Hz, 6H), 2.12 (m, 4H), 2.56 (s, 2H), 4.19 (q, J=14.16 Hz, 4H), and 5.68 (s, 2H). $^{13}$C-NMR (125 MHz, CDCl$_3$), δ: 171.84, 126.31, 124.24, 61.49, 53.16, 30.64, 27.57, 22.54, and 14.27.

Phase Selectivity Studies Procedure

The sample that was to be analyzed (0.12 rug) was dissolved in 12.0 mL of heptane. Then 2 mL of this solution was added to 2 mL of polar solvent (acetonitrile, ethylene glycol diacetate, di(ethylene glycol)monomethyl ether or heptane-saturated DMF). The mixture was sealed and heated to 120° C. to generate a homogeneous solution (in the case of the heptane-acetonitrile system, only partial miscibility occurred). The solution was cooled to room temperature and centrifuged for 1 h at 5° C. to produce a biphasic solution. Part of each phase was then analyzed with a UV-Vis spectroscope. Another portion at each phase was used as a sample for metal analysis.

ICP-MS Digestion Procedure

The sample that was to be analyzed (3-25000 μg) and 4 g of concentrated nitric acid were added to a glass vial. The mixture was heated to 120° C. until most compounds were dissolved. At this point, 4 g of concentrated sulfuric acid was added to the solution at room temperature and heated to 120° C. until all of the compounds were dissolved. The solution was then allowed to stand at room temperature. At this point, the concentrated acidic aqueous solution was diluted with 1% nitric acid solution and the diluted sample solution was analyzed by ICP-MS.

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

REFERENCES

Ahmed M, Barrett A G M, Braddock D C, Cramp S M, Procopiou P A (1999) A recyclable 'boomerang' polymer-supported ruthenium catalyst for olefin metathesis. *Tetrahedron Lett.* 40:8657-8662.

Arduengo A J, Harlow R L, Kline M (1991) A stable crystalline carbene. *J. Am. Chem. Soc.* 113:361-363.

Bergbreiter D E, Li J (2004) Terminally functionalized polyisobutylene oligomers as soluble supports in catalysis. *Chem Commun.* 1:42-43.

Bergbreiter D E, Osburn P L, Smith T, Li C, Frels J D (2003) Using soluble polymers in latent biphasic systems. *J. Am. Chem. Soc.* 125(20)6254-6260.

Bergbreiter D E, Osburn F L, Frels J D (2001) Nonpolar polymers for metal sequestration and ligand and catalyst recovery in thermomorphic systems. *J. Am. Chem. Soc.* 123(44)11105-11106.

Bergbreiter D E, Osburn P L, Wilson A, Sink E M (2000) Palladium-catalyzed C—C coupling under thermomorphic conditions. *J. Am. Chem. Soc.* 122(38)9058-9064.

Bergbreiter D E, Blanton J R, Chandran R, Hein M D, Huang K J, Treadwell D R, Walker S A (1989). *J. Polym. Sci., Part A: Polym. Chem.* 27:4205-4226.

Buchmeiser M R (2000) Homogeneous metathesis polymerization by well-defined group VI and group VIII transition-metal alkylidenes: fundamentals and applications in the preparation of advanced materials. *Chem Rev.* 100(4): 1565-1604.

Chauvin Y (2006) Olefin metathesis: the early days (Nobel Lecture). *Angew Chem. Int. Ed. Engl.* 45(23):3740-3747.

Clavier H, Grela K, Kirschning A, Mauduit M, Nolan S F (2007) Sustainable concepts in olefin metathesis. *Angewandte Chemie International Edition.* 46:6786-6801.

Connon S J, Dunne A M, Blechert S (2002) A self-generating, highly active, and recyclable olefin-metathesis catalyst. *Angew Chem. Int. Ed. Engl.* 41(20):3835-3838.

Dickerson T J, Reed N N, Janda K D (2002) Soluble polymers as scaffolds for recoverable catalysts and reagents. *Chem Rev.* 102(10):3325-3344.

Garber S B, Kingsbury J S, Gray B L, Hoveyda A H (2000) Efficient and recyclable monomeric and dendritic Ru-based metathesis catalysts. *J. Am. Chem. Soc.* 122(34) 8168-8179.

Glorius F (2007) N-heterocyclic carbenes in transition metal catalysis. *Topics in Organometallic Chemistry.* 21:1-20.

Grubbs R H (2006) Olefin-metathesis catalysts for the preparation of molecules and materials (Nobel Lecture). *Angew Chem. Int. Ed. Engl.* 45(23):3760-3765.

Grubbs R H, Tumas W (1989) Polymer synthesis and organotransition metal chemistry. *Science.* 243(4893):907-915.

Hong S H, Grubbs R H (2006) Highly active water-soluble olefin metathesis catalyst. *J. Am. Chem. Soc.* 128(11)3508-3509.

Hong S H, Grubbs R H (2007) Efficient removal of ruthenium byproducts from olefin metathesis products by simple aqueous extraction. *Org. Lett.* 9:1955-1957.

Hongfa C, Tian J, Bazzi H S, Bergbreiter D E (2007) Heptane-soluble ring-closing metathesis catalysts. *Org. Lett.* 9:3259-3261.

Jafarpour L, Nolan S P (2000) Simply assembled and recyclable polymer-supported olefin metathesis catalysts. *Org. Lett.* 2(25):4075-4078.

Kingsbury J S, Hoveyda A H (2005) Regarding the mechanism of olefin metathesis with sol-gel-supported Ru-based complexes bearing a bidentate carbene ligand. Spectroscopic evidence for return of the propagating Ru carbene. *J. Am. Chem. Soc.* 127(12):4510-4517.

Li J, Sung S, Tian J, Bergbreiter D E (2005) Polyisobutylene supports—a non-polar hydrocarbon analog of PEG supports. *Tetrahedron.* 61:12081-12092.

Liddle S T, Edworthy I S, Arnold P L (2007) Anionic tethered N-heterocyclic carbene chemistry. *Chem. Soc. Rev.* 36:1732-1744.

Liu Y-S, Zhao C, Bergbreiter D E, Romo D (1998) Simultaneous deprotection and purification of BOC-amines based on ionic resin capture. *J. Org. Chem.* 63:3471-3473.

Marion N, Díez-González S, Nolan S P (2007) N-heterocyclic carbenes as organocatalysts. *Angewandte Chemie International Edition.* 46:2988-3000.

Nguyen S T, Grubbs R H (1995) The syntheses and activities of polystyrene-supported olefin metathesis catalysts based on C12(PR3)2Ru=CH—CH=CPh2. *J. Organomet. Chem.* 497:195-200.

Romero P E, Piers W E, McDonald R (2004) Rapidly initiating ruthenium olefin-metathesis catalysts. *Angew Chem Int Ed Engl.* 43(45):6161-6165.

Trnka T M, Grubbs R H (2001) The development of L2×2Ru=CHR olefin metathesis catalysts: an organometallic success story. *Acc. Chem. Res.* 34(1):18-29.

Wang H M J, Lin I J B (1998) Facile synthesis of silver(I)-carbene complexes. Useful carbene transfer agents. *Organometallics.* 17:972-975.

Wu P, Fokin V V (2007) Catalytic azide-alkyne cycloaddition: reactivity and applications. *Aldrichimica Acta.* 40:7-17.

Yao Q, Zhang Y (2004) Poly(fluoroalkyl acrylate)-bound ruthenium carbene complex: a fluorous and recyclable catalyst for ring-closing olefin metathesis. *J. Am. Chem. Soc.* 126(1):74-75.

Zeitler K, Mager 1 (2007) An efficient and versatile approach for the immobilization of carbene precursors via copper-catalyzed [3+2]-cycloaddition and their catalytic application. *Advanced Synthesis & Catalysis.* 349:1851-1857.

What is claimed is:

1. A reaction composition comprising:
   a) a nonpolar solvent, wherein the solvent is not latently biphasic;
   b) a catalyst that is complexed to a nonpolar support comprising polyisobutylene, wherein the catalyst-support complex is dissolved in the solvent; and
   c) a substrate molecule dissolved in the solvent, wherein the molecule is a substrate for the catalyst, and wherein the product of a reaction of the molecule with the catalyst is less soluble in the solvent compared to the molecule.

2. The composition of claim 1, wherein the product is completely insoluble in the solvent.

3. The composition of claim 1, wherein the solvent comprises an alkane.

4. The composition of claim 3, wherein the solvent comprises heptane.

5. The composition of claim 1, wherein the catalyst comprises a metal selected from the group consisting of ruthenium, silver and combinations thereof.

6. The composition of claim 1, wherein the catalyst comprises a ruthenium catalyst.

* * * * *